(12) United States Patent
Konya et al.

(10) Patent No.: US 6,355,841 B1
(45) Date of Patent: Mar. 12, 2002

(54) PROCESS FOR PRODUCING β-CAROTENE

(75) Inventors: Naoto Konya, Takatsuki; Shinzo Seko, Toyonaka, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/685,030

(22) Filed: Oct. 10, 2000

(30) Foreign Application Priority Data

Oct. 12, 1999 (JP) .......................................... 11-289312

(51) Int. Cl.⁷ ...................... C07C 315/00; C07C 403/00
(52) U.S. Cl. ............................. 568/32; 568/34; 585/351
(58) Field of Search ............................. 568/28, 32, 34; 585/381

(56) References Cited

U.S. PATENT DOCUMENTS

| | | | | |
|---|---|---|---|---|
| 3,367,985 A | * | 2/1968 | Surmatis et al. | |
| 3,932,546 A | * | 1/1976 | Buchi et al. | |
| 4,105,855 A | * | 8/1978 | Schulz et al. | 560/190 |
| 4,825,006 A | * | 4/1989 | Otetra et al. | 568/32 |
| 5,185,468 A | * | 2/1993 | Mori et al. | 568/31 |
| 5,237,102 A | | 8/1993 | Mori et al. | |
| 6,211,411 B1 | * | 3/2001 | Takhashi et al. | 568/31 |

FOREIGN PATENT DOCUMENTS

| | | |
|---|---|---|
| EP | 0461653 A1 | 12/1991 |
| EP | A20900785 | 10/1999 |
| EP | 1 092 709 * | 4/2001 |
| JP | B2506495 | 4/1996 |
| JP | A8311020 | 11/1996 |

OTHER PUBLICATIONS

Chemla, F. et al., Bull.Soc. Chim. Fr. (1993), vol. 130, pp. 200–205; "A stereo–selective C10+ C10 route to retinal".
Choi, Hojin et al., J.Org. Chem. (1990), vol.64 (21) ; pp. 8051–8053; XP000852477; "Key Structures for Cartenoid Syntheses".
Kurt Bernhard, et al. "Recent advances in the synthesis of achiral carotenoids"Pure & Appl. Chem., vol. 63, No. 1, 1991, pp. 35–44.
Von O. Isler, et al. "Synthesen in der Carotinoid–Reihe"Helvetica Chimica Acta., vol . XXXIX, Fasciculus I, 1956 –No. 27, pp. 249–259.

* cited by examiner

Primary Examiner—Jean F. Vollano

(74) Attorney, Agent, or Firm—Birch, Stewart, Kolasch & Birch, LLP

(57) ABSTRACT

There are disclosed a process for producing a sulfon derivative of formula (1):

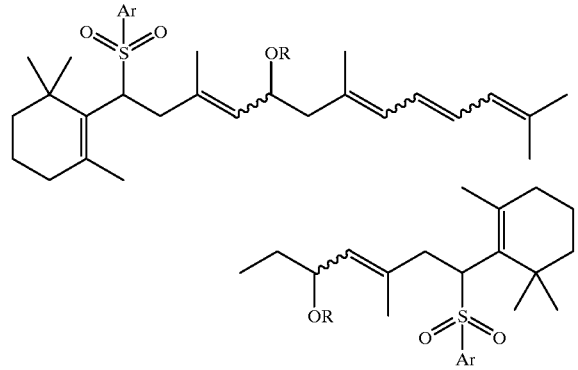

(1)

wherein
Ar represents an aryl group which may be substituted,
R represents a lower alkyl group and the wavy line depicted by

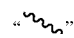

indicates a single bond and stereochemistry relating to a double bond bound therewith is E or Z or a mixture thereof, which process is characterized by reacting an aldehyde derivative of formula (2):

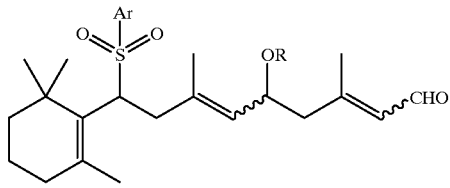

(2)

with phosphonium salt of formula (3):

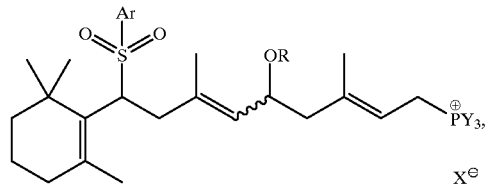

(3)

in the presence of a base; a sulfone derivative of formula (1) and a process for producing a β-carotene using sulfone derivative of formula (1).

8 Claims, No Drawings

PROCESS FOR PRODUCING β-CAROTENE

BACKGROUND OF THE INVENTION

The present invention relates to a process for the production of β-carotene, a carotenoid that is important in the fields of medicines, feed additives and food additives and also to an intermediate of β-carotene.

For the synthesis of β-carotene, which is a symmetric C40 compound, there have been known a method of coupling two C19 compounds and a C2 compound, and a method of coupling two C15 compounds and a C10 compound (e.g., Helv. Chim. Acta, Vol. 39, 249 (1956) or Pure & Appl. Chem., Vol. 63, 35 (1991)). However, these methods were not always satisfactory in that they required to synthesize two different compounds having different carbon numbers and molecular structures. Methods of coupling two C20 compounds as reported in Pure & Appl. Chem., Vol. 63, 35 (1991), Japanese Patent No.2506495 or JP8-311020(Laid-Open unexamined) have also been known, however, these methods are not always practical from an industrial point of view because of multistep reactions to obtain C20 compounds, instability of intermediates, low yield of coupling reaction of said two C20 compounds, or the like.

SUMMARY OF THE INVENTION

An object of the invention is to provide a method for producing β-carotene using a novel intermediate compound.

Further objects of the invention are to provide industrially advantageous two C20 compounds for producing the intermediate compound and methods for producing the two C20 compounds from an inexpensive C10 compound, linalool or geraniol in an industrially advantageous manner.

The present invention provides:

1. a process for producing a sulfone derivative of formula (1):

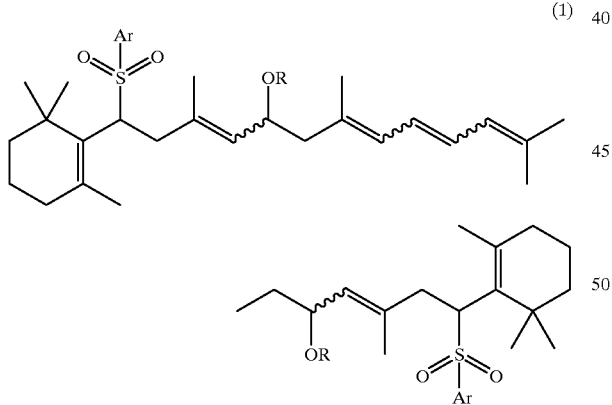

(1)

wherein

Ar represents an aryl group which may be substituted,

R represents a lower alkyl group and the wavy line depicted by

indicates a single bond and stereochemistry relating to a double bond bound therewith is E or Z or a mixture thereof, which comprises reacting an aldehyde derivative of formula (2):

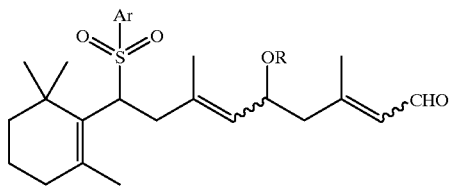

(2)

wherein

Ar, R and the wavy line respectively have the same meanings as defined above, with a phosphonium salt of formula (3):

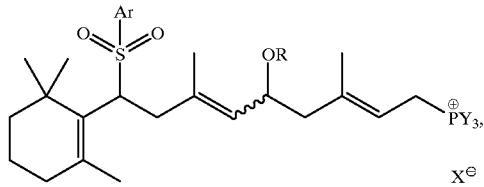

(3)

wherein

Ar, R and the wavy line respectively have the same meanings as defined above, X represents a halogen atom or $HSO_4$, and Y means an lower alkyl group or an optionally substituted phenyl group, in the presence of a base or an epoxide;

2. a sulfone derivative of formula (1) as defined above; and 3. a process for producing β-carotene of formula (4):

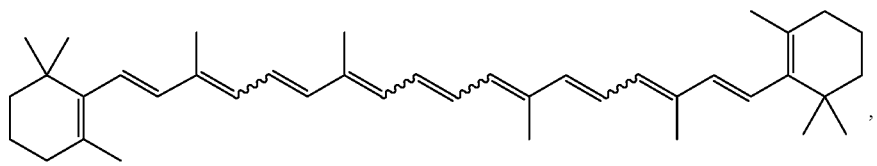

(4)

wherein the wavy line represents the same as defined above, which comprises reacting a sulfone derivative of formula (1) as defined above, with a base.

DESCRIPTION OF THE PREFERRED EMBODIMENTS

The present invention will be hereinafter explained in detail below.

Substituents R and Ar in the chemical formulae of (1) through (7) in the present specification will be explained first.

Examples of the lower alkyl group represented by R in the sulfone derivative (1), aldehyde derivative (2), phosphonium salt (3) and alcohol derivative (7) in the present invention include a (C1–C5) straight or branched chain alkyl group such as a methyl, ethyl, n-propyl, i-propyl, n-butyl, i-butyl, t-butyl group, n-pentyl group, i-pentyl group, neopentyl group and the like. Preferred is a methyl group.

Examples of the aryl group which may be substituted represented by "Ar" include a phenyl group and a naphthyl group, both of which may be substituted with at least one group selected from a C1 to C6 alkyl group(e.g. a methyl, ethyl, n-propyl, i-propyl, n-butyl, s-butyl, i-butyl, t-butyl, n-pentyl, t-amyl, or n-hexyl group), a C1 to C6 alkoxy group(e.g. a methoxy, ethoxy, n-propoxy, i-propoxy, n-butoxy, s-butoxy, i-butoxy, t-butoxy, n-pentyloxy, t-amyloxy, or n-hexyloxy group), a halogen atom and a nitro group.

Preferred Aryl Group is a Tolyl Group.

Specific examples of the optionally substituted aryl group include a phenyl, naphthyl, o-tolyl, m-tolyl, p-tolyl, o-methoxyphenyl, m-methoxyphenyl, p-methoxyphenyl, o-chlorophenyl, m-chlorophenyl, p-chlorophenyl, o-bromophenyl, m-bromophenyl, p-bromophenyl, o-iodophenyl, m-iodophenyl, p-iodophenyl, o-fluorophenyl, m-fluorophenyl, p-fluorophenyl, o-nitrophenyl, m-nitrophenyl and p-nitrophenyl group.

Next, a description will be made to the process for producing a sulfone derivative of formula (1) which comprises reacting an aldehyde derivative of formula (2) with a phosphonium salt of formula (3) in the presence of a base or an epoxide.

Specific examples of the aldehyde derivative of formula (2) include an aldehyde derivative of formula (2), wherein Ar is a p-tolyl group and R is a methyl group, and aldehyde derivatives of formula (2), wherein Ar is a p-tolyl group and R represents any one of specific C2–C4 alkyl groups as described above. Further specific examples thereof include aldehyde derivatives of formula (2), wherein the p-tolyl group is replaced by other specific groups as described above for "Ar" in the above-described specific aldehyde derivatives.

The aldehyde derivative (2) can be obtained by a process as shown in Scheme 1.

In the phosphopnium salt of formula (3), a halogen atom represented by X include a chlorine atom, bromine atom and iodine atom.

Examples of the lower alkyl group represented by Y include a C1–C6 alkyl group such as a methl, ethyl, n-propyl, i-propyl, sec-butyl, n-butyl, i-butyl, n-pentyl, or the like.

Examples of the optionally substituted phenyl group represented by Y include a phenyl group which may be substituted with a C1–C3 alkyl (e.g. a methyl, ethyl, n-propyl, or i-propyl group) or a C1–C3 alkoxy group (e.g. a methoxy, ethoxy, n-propoxy, or i-propoxy group).

Specific examples of a group of formula: $PY_3$ in the phosphonium salt of formula (3) include triethylphosphine, tripropylphosphine, tributylphosphine, tripentylphosphine, trihexylphosphine, triphenylphosphine, tri-(o-tolyl) phosphine and the like.

Specific examples of the phosphonium salt (3) include a phosphonium salt (3), wherein "Ar" and R have the same meaning as defined for specific examples of the aldehyde derivative of formula (2) and Y is a phenyl group and X is chlorine, and further examples of compounds of formula (3), wherein Y represents any one of the groups as specified for Y above in place of the phenyl group above. In addition to these phosphonium salt (3), yet further examples thereof include phosphonium salts of formula (3), wherein X represents bromine, iodine or $HSO_4$ in place of chlorine in the specified compounds above, and the like.

The amount of the phosphonium salt (3) to be used is usually 0.5 to 2.0 moles, preferably, 0.8 to 1.2 per mole of the aldehyde derivative (2).

There is no particular limitation as to the base used in the above reaction of the aforementioned phosphonium salt (3) with the aldehyde derivative (2) as long as it does not adversely affect the reaction.

Examples of the base include an alkali metal alkoxide such as potassium methoxide, potassium ethoxide, potassium n-butoxide, potassium t-butoxide, sodium methoxide, sodium ethoxide, sodium n-butoxide, or sodium t-butoxide and an alkali metal hydroxide such as potassium hydroxide or sodium hydroxide. An epoxide such as an ethylene oxide or 1,2-butene oxide may be used instead of the base.

The amount of the base or epoxide to be used is usually 1 to 5 moles per mol the phosphonium salt of formula (3).

Reacting of an aldehyde derivative of formula (2) with a phosphonium salt of formula (3) in the presence of a base or an epoxide is usually conducted in an organic solvent.

Examples of the solvent include a hydrocarbon solvent such as n-hexane, cyclohexane, n-pentane, n-heptane, toluene or xylene, a halogenated hydrocarbon solvent such as chloroform, dichloromethane, 1,2-dichloroethane, monochlorobenzene, o-dichlorobenzene or α, α, α-trifluorotoluene, an aprotic polar solvent such as N,N-dimethylformamide, dimethylsulfoxide, acetonitrile, N,N-dimethylacetamide or hexamethylphosphoric triamide and an ether solvent such as 1,4-dioxane, tetrahydrofuran or anisole.

The reaction may also be conducted in a two phase system of an organic solvent immiscible with water such as the hydrocarbon solvent, the halogenated hydrocarbon solvent or the like as referred to above and water.

The reaction temperature is usually in a range of about −10° C. to 150° C., preferably 0° C. to 100° C.

After completion of the reaction, the reaction mixture is usually subjected to post-treatments which include optionally filtration, washing, phase separation and/or evaporation to give the sulfone derivative (1), which may be further purified by column chromatography or recrystallization, if necessary.

The phosphonium salt (3) can be obtained by a process which comprises reacting an alcohol derivative of formula (7):

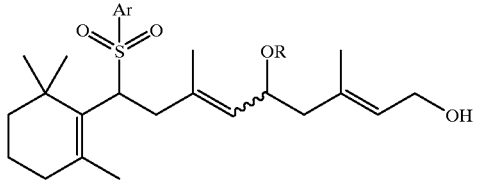

(7)

wherein Ar, R and the wavy line respectively have the same meanings as defined above, with a salt of a tertiary phosphine compound of formula: $PY_3$ and a protonic acid, or with a tertiary phosphine compound of formula: $PY_3$, in the presence of a protonic acid, wherein Y represents the same as defined above.

Examples of the tertiary phosphine compound include a triphenylphosphine compound of which phenyl group may be substituted with a C1–C3 alkyl or a C1–C3 alkoxy group, and a tri(C1–C6)alkylphosphine.

Specific examples of the triphenylphosphine compound include triphenylphosphine, tri-(o-tolyl)phosphine and the like.

Specific examples of said trialkylphosphine include triethylphosphine, tripropylphosphine, tributylphosphine, tripentylphosphine, trihexylphosphine and the like.

Examples of the protonic acid include hydrogen chloride, hydrogen bromide, hydrogen iodide and sulfuric acid Examples of the salt of the tertiary phosphine compound and a protonic acid used in the above reaction include triphenylphosphine hydrochloride, triphenylphosphine hydrobromide or triphenylphosphine hydroiodide.

Examples of the protonic acid allowed to coexist with the tertiary phosphine compound include hydrogen chloride, hydrogen bromide, hydrogen iodide and sulfuric acid.

The amount of the tertiary phosphine compound or its salt with a protonic acid is usually about 0.7 to 2 moles per mol of the alcohol derivative (7). The amount of the protonic acid allowed to coexist with the tertiary phosphine compound is usually about 0.7 to 2.0 moles per mol of the alcohol derivative (7).

The reaction is usually conducted in an organic solvent, examples of which include those specified for the reaction of aldehyde derivative of formula (2) and a phosphonium derivative (3) above, and an alcohol solvent such as methanol or ethanol.

The reaction temperature is usually in a range of 10° C. to 50° C.

The resulting phosphonium salt (3) may be isolated after the reaction, alternatively it may be used as it is in the subsequent reaction without being isolated.

β-carotene of formula (4) can be produced by a process which comprises reacting the sulfone derivative (1) with a base.

Example of the base to be used in the this reaction include an alkali metal hydroxide, an alkali metal hydride and an alkali metal alkoxide. Specific examples thereof include sodium hydroxide, potassium hydroxide, sodium hydride, potassium hydride, sodium anethoxide, potassium methoxide, sodium ethoxide, potassium ethoxide, sodium t-butoxide, potassium t-butoxide and the like. The amount of the base is usually about 2 to 30 moles, preferably 4 to 25 moles per mol of the sulfone derivative (1).

The reaction is usually conducted in an organic solvent, examples of which include those described above for the production process of the phosphonium derivative (3) above.

The reaction temperature is usually in a range of -78° C. to the boiling point of the solvent to be used.

After completion of the reaction, the reaction mixture is usually subjected to post-treatments which include optionally filtration, washing, phase separation and/or evaporation as described above to give β-carotene, which may be further purified by column chromatography or recrystallization, if necessary.

Since β-carotene is liable to be oxidized, said post-treatments are preferably carried out in an inert atmosphere, for example, in a atmosphere of nitrogen or argon, and an antioxidant such as BHT(di-t-butylhydroxytoluene) may be added to the reaction mixture or a solution thereof.

The alcohol derivative (7), which may be a mixture of geometrical isomers of E and Z, a racemate or an optically active isomer can be used in the present process.

The alcohol derivative (7) above can be readily synthesized from linalool or geraniol, which is available at relatively low cost, according to the route as shown by the Scheme 1 described below. A method for the synthesis of the cyclic sulfone (5) is described in JP11-222479(Laid-Open, unexamined). The sulfone (6) can be derivatized by deacylation followed by selective alkylation of a secondery alcohol group to the alcohol derivative (7), which can be oxidized to aldehyde derivative (3) as shown in the following scheme and reference examples.

Scheme 1

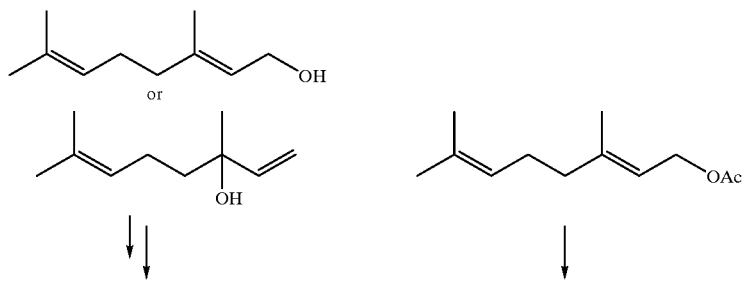

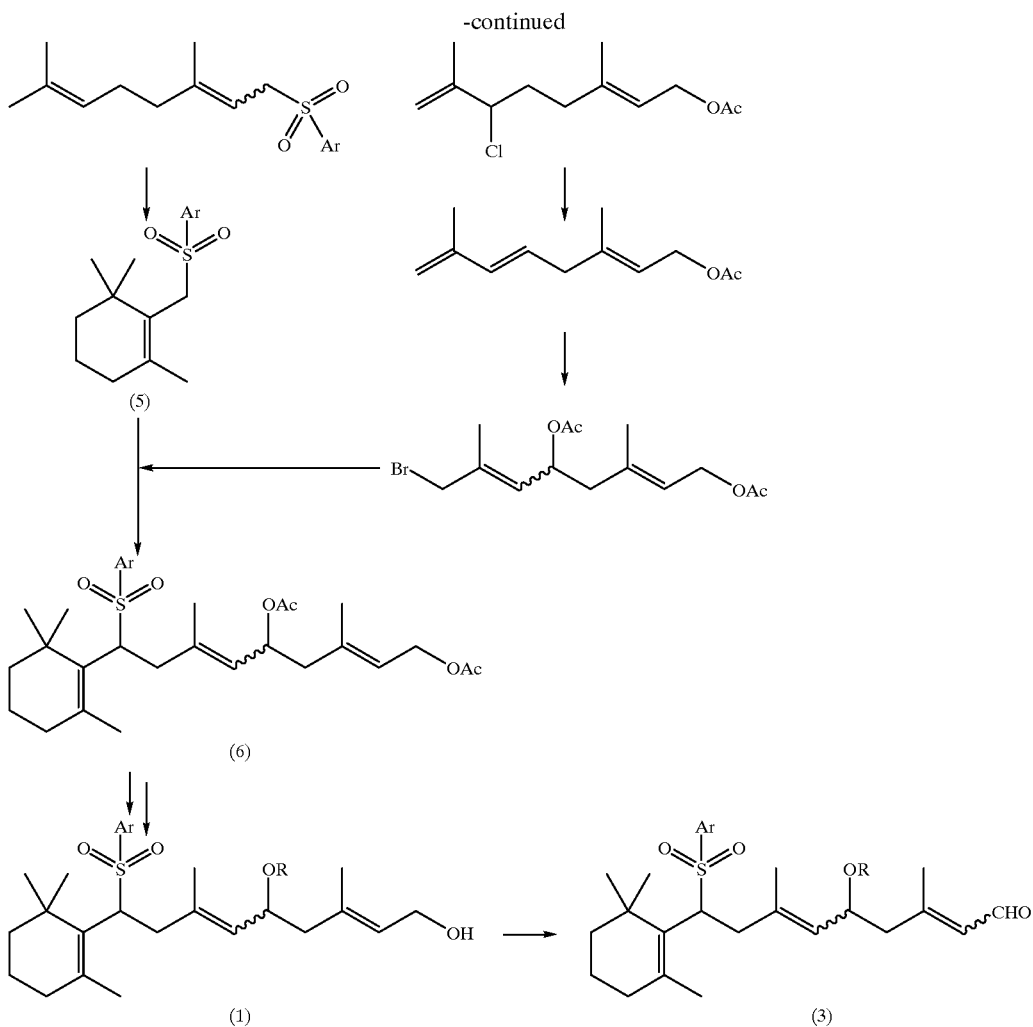

According to the process of the present invention, β-carotene which is an important carotenoid in the fields of medicines, feed additives and food additives can be produced from readily available linalool or geraniol in an industrially advantageous manner.

EXAMPLES

The present invention will be explained in more detail by way of examples, which are not intended to be limiting of the present invention. Each structural formula of the compounds (I) to (V) used in the Examples is shown in the Scheme 2 below.

Example 1

1.129 g (2.38 mmol) of methoxy alcohol (I) was dissolved in 20 ml of methanol, to which was added 0.926 g of triphenylphosphine hydrobromide and the mixture was stirred at an ambient temperature for 24 hours. The reaction solution was evaporated to obtain 1.95 g of a crude phosphonium salt (III). The resulting crude product was used in the subsequent reaction as it is.

$^1$H-NMR δ(CDCl$_3$); 0.60–1.10(6 H,m), 1.10–1.70(10 H,m), 1.70–2.30(6 H,m), 2.40(3 H,br), 2.50–3.50(6 H,m), 3.80–4.10(2 H,m), 4.30–4.70(1 H,m), 4.70–5.30(2 H,m), 5.30–6.30(1 H,m), 7.20–8.00(19 H,m).

Example 2

258 mg (0.545 mmol) of methoxy aldehyde (II) was dissolved in 1.2 ml of dichloromethane, to which was added 1.2 ml of 2M sodium 25 hydroxide. 1.0 ml of dichloromethane solution containing 591 mg (0.74 mmol) of the crude phosphonium salt (III) was added thereto under stirring over about 20 min and thereafter stirred at room temperature for 24 hours. Water was added to the reaction solution and extracted with chloroform, dried over anhydrous magnesium sulfate, evaporated to give a crude product, which was purified by silica gel column chromatography to give methoxy sulfone (IV) as a pale yellow oil containing E,Z and diastereomers in a yield of 68%.

$^1$H-NMR δ(CDCl$_3$); 0.70–0.90(6 H,m), 0.90–1.12(6 H,m), 1.31–1.65(8 H,m), 1.43(6 H,br), 1.67(6 H,s), 1.92–2.38(8 H,m), 2.01(6 H,br), 2.44(6 H,s), 2.55–2.85(2 H,m), 2.85–3.05(2 H,m), 3.05–3.25(6 H,m), 3.80–4.00(4 H,m), 4.95–5.20(2 H,m), 5.80–6.00(1 H,m), 6.00–6.15(1 H,m), 6.15–6.50(2 H,m), 7.20–7.40(4 H,m), 7.60–7.85(4 H,m).

Example 3

91 mg (0.1 mmol) of methoxyaldehyde (IV) was dissolved in 2 ml of tetrahydrofuran, to which was added 105 mg (1.5 mmol) of potassium methoxide and refluxed for 6 hours. After being cooled to room temperature, water was added to the reaction solution and extracted with chloroform, dried over anhydrous magnesium sulfate, evaporated to give 58 mg of a crude product, which was further purified by silica gel column chromatography to give β-carotene (V) as a E and Z mixture in a yield of 69%.

Example 4

535 mg (1.13 mmol) of the methoxyaldehyde (II) was dissolved in 3 ml of dichloromethane, to which was added 2.5 ml of 2M aqueous sodium hydroxide solution. 2 ml of dichloromethane solution containing 1129 mg (1.41 mmol) of the crude phosphonium salt (III) was added thereto under stirring over about 25 min and thereafter stirred at room temperature for 24 hours. Water was added to the reaction solution and extracted with chloroform, dried over anhydrous magnesium sulfate, evaporated to give 1.619 g of methoxy sulfone (IV). Obtained crude Methoxy sulfone (IV) was dissolved in 20 ml of tetrahydrofuran and 1.19 g (17 mmol) of potassium methoxide was added thereto and stirred at room temperature for 2 hours and refluxed for 6 hours. After cooling the reaction solution to room temperature, water was added thereto and extracted with chloroform and dried over anhydrous magnesium sulfate. Then the organic solution was evaporated to give 1.06 g of a crude product, which was purified by silica gel column chromatography to give β-carotene (V) as a E and Z mixture in a yield of 69% from methoxyaldehyde (II).

$^1$H-NMR δ(CDCl$_3$); 0.83–1.03(6 H,m), 1.33–1.61(2 H,m), 1.38(3 H,s), 1.43(3 H,s), 1.70(3 H,s), 1.90–2.18(7 H,m), 2.44(3 H,s), 2.52–2.62(1 H,m), 2.80–2.95(1 H,br), 2.95–3.13(1 H,m), 3.77–3.84(1 H,m), 3.90(1 H,t,J=7 Hz), 4.03(2 H,d,J=7 Hz), 5.33–5.36(1 H,m), 5.48–5.52(1 H,t,J=7 Hz), 7.30(2 H,d,J=8 Hz), 7.74(2 H,d,J=8 Hz).

Reference Example 2

5.48 g (11.9 mmol) of diol compound (b) was dissloved in 50ml of methanol, to which was added 114 mg (0.6 mmol) of p-toluenesulfonic acid. After stirring 24 hours at room temperature, 114 mg (0.6 mmol) of p-toluenesulfonic acid was further added thereto and stirred at room temperature for 24 hours. After completion of the reaction, a saturated aqueous sodium hydrogen carbonate solution was added thereto and extracted with ether, extract was washed with saturated aqeous sodium chloride solution, dried over anhydrous magnesium sulfate, filtrate was evaporated to gave methoxyalcohol (I) containing E,Z and diastereomers as a pale yellow oil in a yield of 76%.

$^1$H-NMR δ(CDCl$_3$); 0.70–1.10(6 H,m), 1.30–1.65(8 H,m), 1.65–1.75(3 H,br), 1.90–2.40(6 H,m), 2.44(3 H,s),

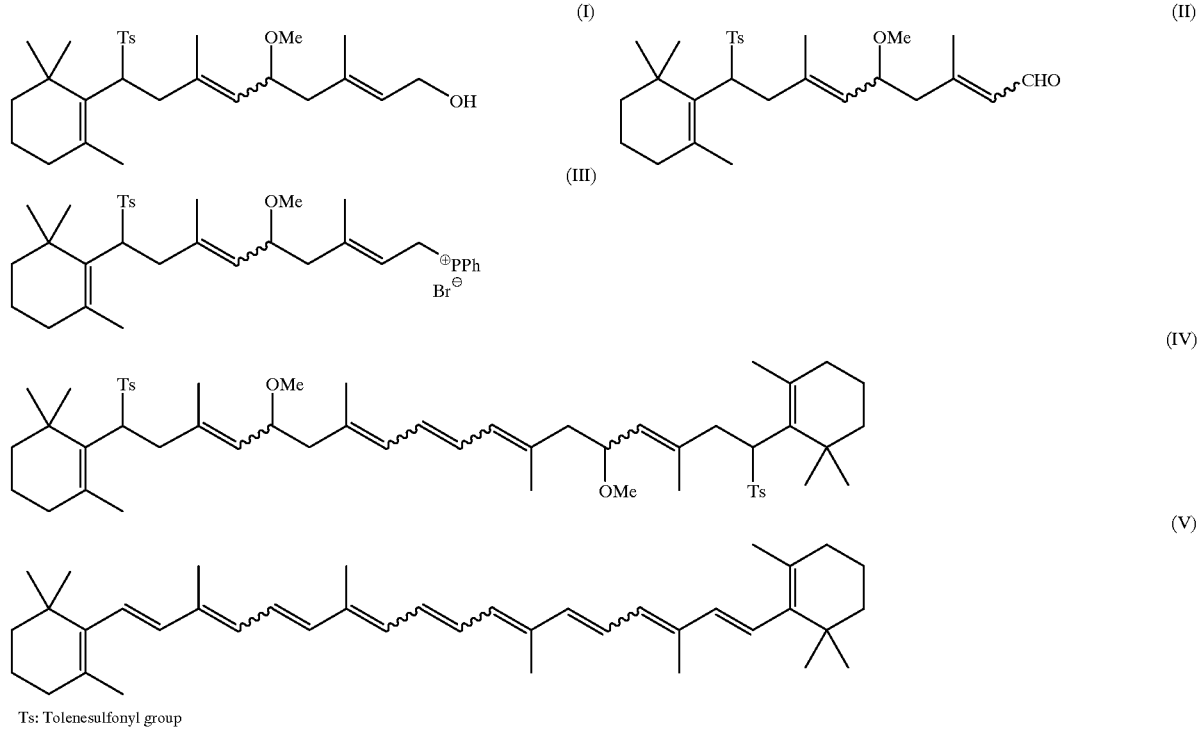

Ts: Tolenesulfonyl group

Chemical formulae of the compounds (a), (b), (I) and (II) used in the Reference Examples are shown in Scheme 3 below.

Reference Example 1

200 mg (0.37 mmol) of sulfone compound (a) was dissolved in 5 ml of methanol, to which was added 0.11 g (0.74 mmol) of 27% sodium hydroxide and the mixture was stirred at 25° C. for 4 hours. After the reaction, reaction was quenched with saturated aqueous ammonium chloride solution and extracted with ethyl acetate. Combined organic layers were washed with saturated aqueous sodium chloride solution and dried over anhydrous magnesium sulfate, then evaporated to give diol compound (b) as a E,Z and diastereomer mixture in a yield of 95%.

2.60–2.80(1 H,m), 2.90–3.15(1 H,m), 3.15–3.25(3 H,m), 3.80–4.00(2 H,m), 4.00–4.20(2 H,m), 5.00–5.20(1 H,m), 5.35–5.50(1 H,m), 7.20–7.40(2 H,m), 7.70–7.90(2 H,m).

Reference Example 3

1.3 g of manganese dioxide was added to a solution of 1.42 g (2.99 mmol) of methoxy alcohol(I) in 10 ml of dichloromethane, and the resulting solution was stirred at room temperature for 8 hours. After 1.3 g of manganese dioxide was further added to the reaction mixture and stirred at room temperature for 12 hours, reaction mixture was diluted with ether, dried over anhydrous magnesium sulfate, filtrate was evaporated to give a crude product. Obtained crude product was purified by silica gel column chromatography to give methoxyaldehyde (II) as a pale yellow oil containing E, Z and diastereomers in a yield of 91%

¹H-NMR δ(CDCl₃); 0.75–1.05(6 H,m), 1.30–1.60(8 H,m), 1.90–2.45(3 H,m), 2.02(3 H,d,J=1.5 Hz), 2.18(3 H,t, J=1.5 Hz), 2.45(3 H,s), 2.71(1 H,dd,J=7 Hz,15 Hz), 3.04(1 H,dd,J=6 Hz,15 Hz), 3.18(3 H,d,J=15 Hz), 3.85–3.95(1 H,m), 3.95–4.05(1 H,m), 5.00–5.10(1 H,m), 5.80–5.90(1 H,m), 7.20–7.35(2 H,m), 7.65–7.85(2 H,m), 9.98(1 H,d,J=8 Hz).

Scheme 3

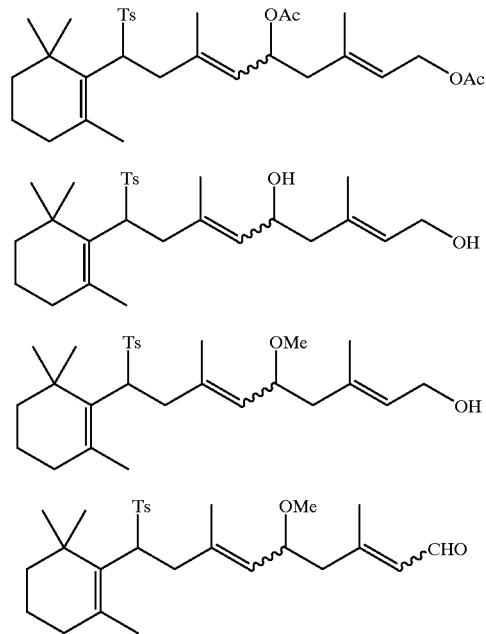

Ts: Tolenesulfonyl group

What is claimed is:

1. A process for producing a sulfone derivative of formula (1):

(1)

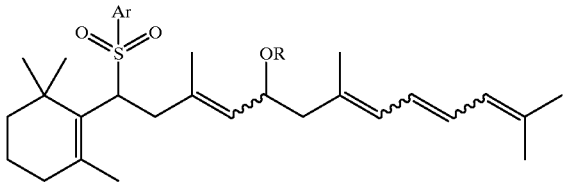

-continued

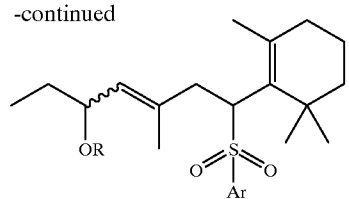

wherein

Ar represents an aryl group which may be substituted,

R represents a lower alkyl group and the wavy line depicted by

"〰"

indicates a single bond and stereochemistry relating to a double bond bound therewith is E or Z or a mixture thereof, which comprises reacting an aldehyde derivative of formula (2):

(2)

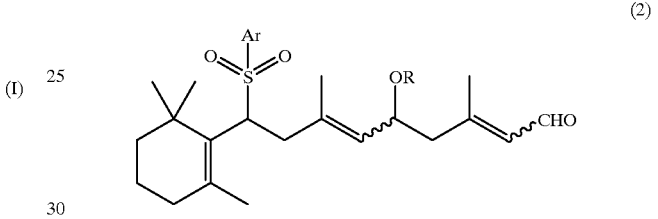

wherein Ar, R and the wavy line respectively have the same meanings as defined above, with a phosphonium salt of formula (3):

(3)

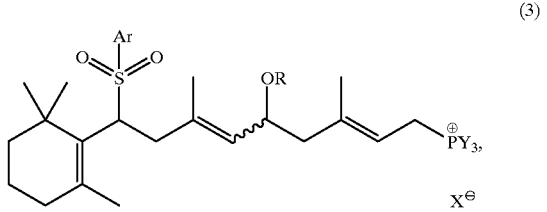

wherein

Ar, R and the wavy line respectively have the same meanings as defined above, X represents a halogen atom or HSO₄, and Y means an lower alkyl group or an optionally substituted phenyl group, in the presence of a base or an epoxide.

2. A sulfone derivative of formula (1) as defined in claim 1.

3. A process for producing β-carotene of formula (4):

(4)

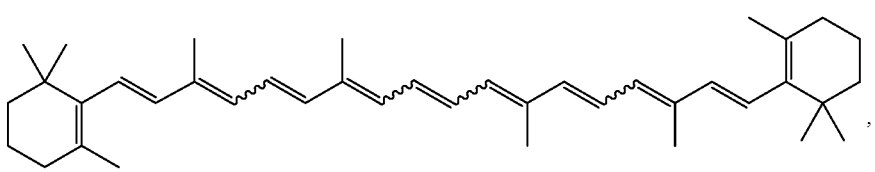

wherein the wavy line depicted by

indicates a single bond and stereochemistry relating to a double bond bound therewith is E or Z or a mixture thereof, which comprises reacting a sulfone derivative of formula (1):

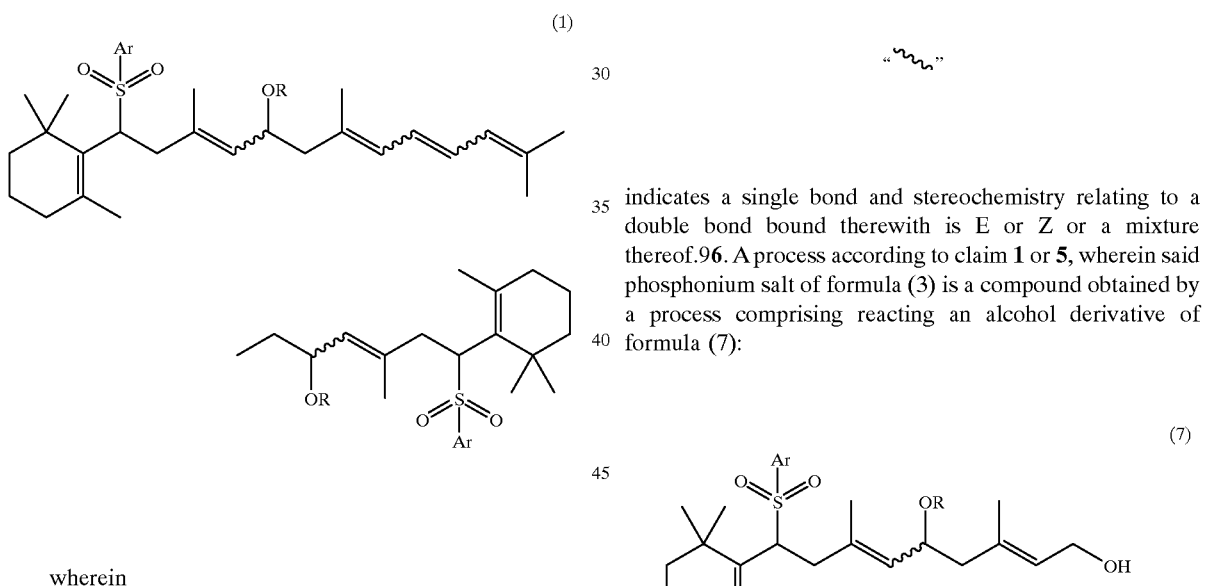

wherein

Ar represents an aryl group which may be substituted, R represents a lower alkyl group and the wavy line depicted by

indicates a single bond and stereochemistry relating to a double bond bound therewith is E or Z or a mixture thereof, with a base. 94. A process according to claim 1, wherein R represents a (C1–C5) alkyl group, and Ar represents a phenyl group or a naphthyl group, both of which may be substituted with at least one group selected from a (C1–C6) alkyl group, a (C1–C6) alkoxy group, a halogen atom or a nitro group. 95. A process according to claim 1, which further comprises the step of reacting the sulfone derivative of formula (1) with a base to produce a β-carotene of formula (4):

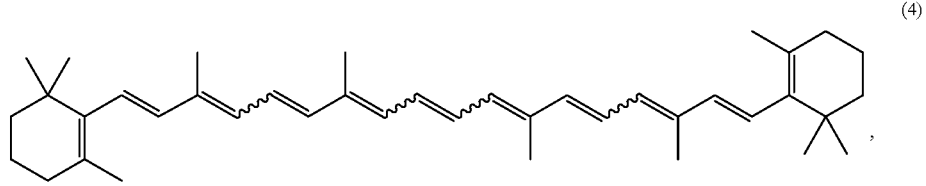

wherein the wavy line depicted by

indicates a single bond and stereochemistry relating to a double bond bound therewith is E or Z or a mixture thereof. 96. A process according to claim 1 or 5, wherein said phosphonium salt of formula (3) is a compound obtained by a process comprising reacting an alcohol derivative of formula (7):

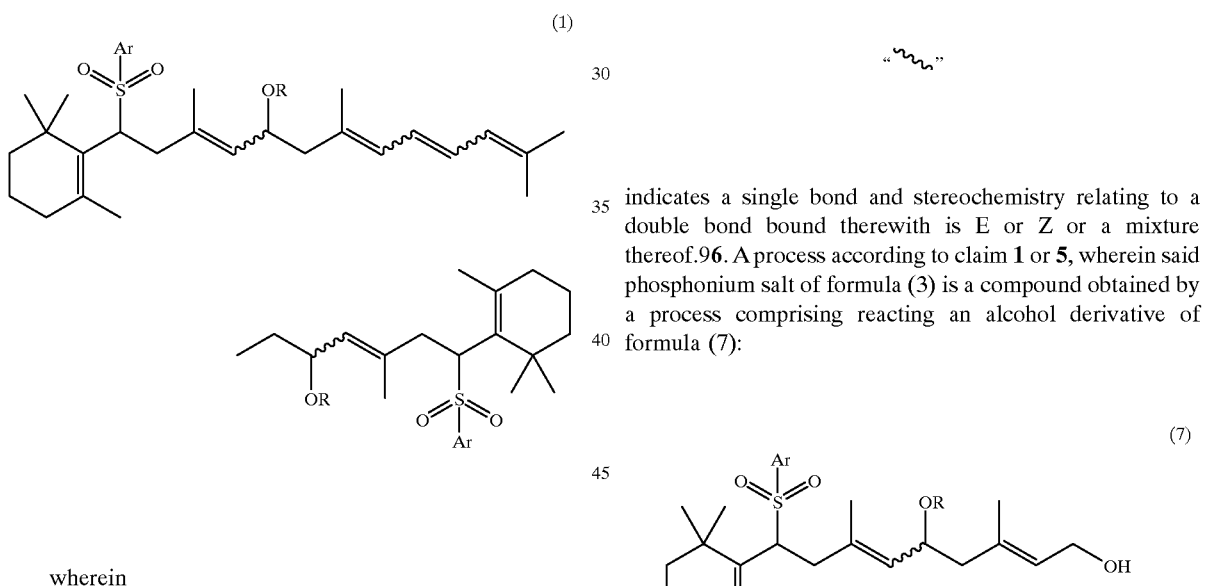

wherein Ar, R and the wavy line respectively have the same meanings as defined in connection with formula (3), with a salt of a tertiary phosphine compound of formula: PY3 and a protonic acid, or with a tertiary phosphine compound of formula: PY3, in the presence of a protonic acid, wherein Y represents the same as defined in connection with formula (3) and said protonic acid is a protonic acid selected from hydrogen chloride, hydrogen bromide, hydrogen iodide or sulfuric acid. 97. A process according to claim 6, wherein Y is a phenyl group. 98. A process according to claim 3 or 5, wherein said base is an alkali metal hydroxide or alkali metal alkoxide.

* * * * *